United States Patent [19]

Korsgaard et al.

[11] Patent Number: 5,886,021

[45] Date of Patent: Mar. 23, 1999

[54] USE OF 3,4-DIPHENYL CHROMANS FOR THE MANUFACTURE OF A PHARMACEUTICAL COMPOSITION FOR VASODILATORY TREATMENT OR PROPHYLAXIS

[75] Inventors: Niels Korsgaard, Værløse; Michael Shalmi, København V; Jan Ulrik Weis, Virum; Birgitte Hjort Guldhammer, Hillerød, all of Denmark

[73] Assignee: Novo Nordisk A/S, Bagsvaerd, Denmark

[21] Appl. No.: 912,802

[22] Filed: Aug. 18, 1997

Related U.S. Application Data

[63] Continuation of Ser. No. 585,011, Jan. 11, 1996, abandoned.

[30] Foreign Application Priority Data

Jan. 20, 1995 [DK] Denmark ................................. 0067/95
Jun. 30, 1995 [DK] Denmark ................................. 0775/95

[51] Int. Cl.$^6$ ........................... A61K 31/40; A61K 31/35
[52] U.S. Cl. ........................................... 514/422; 514/456
[58] Field of Search ..................................... 514/422, 456

[56] References Cited

U.S. PATENT DOCUMENTS

| | | | |
|---|---|---|---|
| 3,340,276 | 9/1967 | Carney et al. | 260/345.2 |
| 3,822,287 | 7/1974 | Bolger | 260/326.5 |
| 4,447,622 | 5/1984 | Salman et al. | 548/525 |
| 5,280,040 | 1/1994 | Labroo et al. | 514/422 |

OTHER PUBLICATIONS

Chak et al., "Acute Toxicity & Pharmacology of Centchroman", Indian Journal of Experimental Biology, vol. 15, Dec. 1977, pp. 1159–1161.

Ray et al., "An X–ray Crystallographic Study of the Nonsterodial Contraceptive Agent Centchroman", J. Med. Chem. Soc., vol. 37, pp. 696–700(1984).

Dhawan et al., Anti–inflammatory And Some Other Pharmacological Effects of 3,4–trans–2,2–dimethyl–3phenyl–4[p β–pyrrolidinoethoxy)–phenyl]–7–methoxy–chroman (Centchroman), Br. Pharmac. (1973), vol. 49, pp. 64–73.

Grant et al., Grant & Hackh's Chemical Dictionary, Fifth Edition, McGraw–Hill Book Company(1985).

Primary Examiner—Raymond Henley, III
Attorney, Agent, or Firm—Steve T. Zelson; Cheryl H. Agris; Carol E. Rozek

[57] ABSTRACT

The present invention provides novel uses of compounds of general formula I

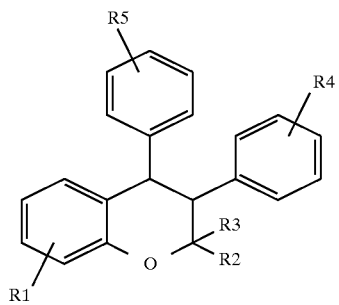

wherein $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or lower alkyl, or as a pharmaceutically acceptable salt thereof in combination with a pharmaceutically acceptable carrier for the manufacture of a pharmaceutical composition for vasodilatory treatment or prophylaxis.

17 Claims, No Drawings

5,886,021

USE OF 3,4-DIPHENYL CHROMANS FOR THE MANUFACTURE OF A PHARMACEUTICAL COMPOSITION FOR VASODILATORY TREATMENT OR PROPHYLAXIS

This application is a continuation of application Ser. No. 08/585,011 filed Jan. 11, 1996, now abandoned which claims priority of Danish applications Ser. Nos. 0067/95 and 0775/95 filed Jan. 20, 1995 snf Jun. 30, 1995, the contents of which are fully incorporated herein by reference.

FIELD OF THIS INVENTION

The present invention relates to the use of compounds of the general formula I for the vasodilatory treatment of patients suffering from, e.g. cerebral ischaemia, angina pectoris or Raynaud's syndrome, and prophylaxis hereof. The present invention also embraces pharmaceutical compositions comprising these compounds and methods of using the compounds and their pharmaceutical compositions.

BACKGROUND OF THIS INVENTION

Vasodilator drugs are used in several conditions involving tissue ischemia with the most important indication being angina pectoris. Atherosclerosis is involved in most cases of angina pectoris. In recent years a number of studies have revealed important information about the effects of estrogens on the cardiovascular system. Experiments in animals (Haarbo J et al. J Clin Invest 1991; 87:1294–1279) and epidemiologic studies in humans (PEPI trial, JAMA 1995; 273:199–208) have demonstrated that estrogens possess antiatherogenic properties and it has been speculated that the decreased cardiovascular morbidity and mortality seen in women between 35 and 50 compared to men, is due to an intact ovarian function with the production of estrogens. It has also been demonstrated that estrogens possess vasodilator properties, at least when administered in test systems in pharmacological doses. Estrogens and estrogen receptor stimulation may therefore have a dual mechanism which may act synergistically on the pathologic mechanisms involved in tissue ischemia.

Recent studies (Writing group for the PEPI trial, JAMA 273:199, 1955) confirm that oral estrogen taken alone or in combination with medroxy-progesterone acetate or micronized progesterone is associated with a beneficial effect on the risk of developing cardiovascular disease. However, estrogen is also known to have adverse effects on endometrium and perhaps breast tissue by increasing the frequency of malignancies in these areas after prolonged treatment.

Thus, there is a need for a new compound which has the beneficial vasodilatory effect of estrogen, but without introducing significant effects on the reproductive tissues.

Centchroman is a non-steroidal compound known to have antiestrogenic activity. It is in use in India as an oral contraceptive (see, for example, Salman et al., U.S. Pat. No. 4,447,622; Singh et al., Acta Endocrinol. (Copenh) 126 (1992), 444–450; Grubb, Curr. Opin. Obstet. Gynecol. 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int. J. Cancer 43 (1989), 781–783). Recently, centchroman as a racemate has been found potent as a cholesterol lowering pharmaceutical expressed by a significant decrease of the serum concentrations (S. D. Bain et al., J. Min. Bon. Res. 9 (1994), 394).

U.S. Pat. No. 5,280,040 describes methods and pharmaceutical compositions for reducing bone loss using 3,4-diarylchromans and their pharmaceutically acceptable salts.

One object of the present invention is to provide compounds which can effectively be used in the vasodilatory treatment or prophylaxis of e.g. cerebral ischaemia, angina pectoris or Raynaud's syndrome.

BRIEF DESCRIPTION OF THIS INVENTION

It has, surprisingly, been found that compounds of the general formula I as stated in claim 1 can be used in the vasodilatory treatment or prophylaxis of e.g. cerebral ischaemia, angina pectoris or Raynaud's syndrome.

DETAILED DESCRIPTION OF THIS INVENTION

The present invention is based in part on the discovery that a representative 3,4-diarylchroman, centchroman (3,4-trans-2,2-dimethyl-3-phenyl-4-[4-(2-(pyrrolidin-1-yl)ethoxy)phenyl]-7-methoxychroman) is an effective vasodilatory drug against e.g. cerebral ischaemia, angina pectoris or Raynaud's syndrome, inter alia in rats. Centchroman is a racemic mixture. These animal models are generally recognized models of e.g. cerebral ischaemia, angina pectoris or Raynaud's syndrome. These data thus indicate that the 3,4-diarylchromans of formula I are useful as therapeutic and preventive agents against e.g. cerebral ischaemia, angina pectoris or Raynaud's syndrome. The above indications relate to mammals, including primates such as humans.

Within the present invention, compounds of formula I as stated in claim 1 are administered as vasodilatory drugs against e.g. cerebral ischaemia, angina pectoris or Raynaud's syndrome. Within formula I, $R^1$, $R^4$ and $R^5$ are individually hydrogen, halogen, trifluoromethyl, lower alkyl, lower alkoxy or (tertiary amino)(lower alkoxy); and $R^2$ and $R^3$ are individually hydrogen or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. The tertiary amino radical may be a N,N-dialkylamine such as a N,N-dimethylamino, N,N-diethylamino, N,N-dipropylamino and N,N-dibutylamino or a polymethyleneimine, e.g., piperidine, pyrrolidine, N-methylpiperazine or morpholine. Herein, the term "(tertiary amino)(lower alkoxy)" is a lower alkoxy group which is substituted by a tertiary amino group. Preferred compounds include those in which $R^1$ is lower alkoxy; $R^2$ and $R^3$ are lower alkyl, especially methyl; $R^4$ is hydrogen; and $R^5$ is (tertiary amino)(lower alkoxy) of the polymethyleneimine type. Within particularly preferred embodiments, $R^1$ is in the 7-position and is lower alkoxy, particularly methoxy; each of $R^2$ and $R^3$ is methyl, $R^4$ is hydrogen, and $R^5$ is in the 4-position and is a (tertiary amino)(lower alkoxy) radical such as 2-(pyrrolidin-1-yl) ethoxy. To be included by this invention are all pharmaceutically acceptable salts of the mentioned compounds of formula I.

It is preferred to use the compounds of formula I in the transconfiguration. These compounds may be used as racemic mixtures, or the isolate stereoisomers, e.g. d- or l-enantiomers, may be used. The trans-d-enantiomers are more preferred.

A particularly preferred compound for use within the present invention is centchroman consisting of l-centchroman and d-centchroman. Probably, l-centchroman has the formula IV

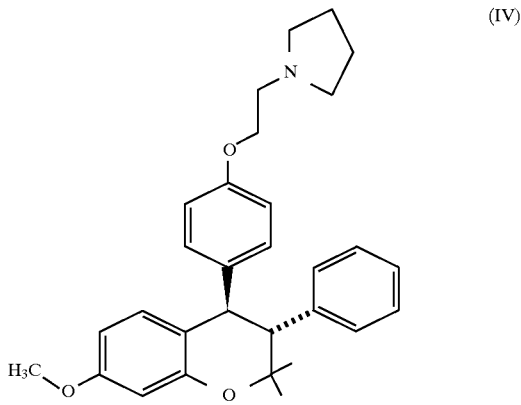

3,4-diarylchromans are prepared according to known methods, such as those disclosed in U.S. Pat. No. 3,340,276 to Carney et al., U.S. Pat. No. 3,822,287 to Bolger, and Ray et al., *J. Med. Chem.* 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. If $R^2$ is different from $R^3$ and $R^4$ is different from $R^5$, the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans of formula I and their salts are useful as vasodilatory drugs within the field of human and veterinary medicine, for example, in the treatment or prophylaxis of patients suffering from e.g. cerebral ischaemia, angina pectoris or Raynaud's syndrome. For use within the present invention, 3,4-diarylchromans of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in *Remington's Pharmaceutical Sciences*, Gennaro, ed., Mack Publishing Co., Easton, Pa., 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant vasodilatory effect against e.g. cerebral ischaemia, angina pectoris or Raynaud's syndrome. Such amounts will depend, in part, on the particular condition to be treated, age, weight, and general health of the patient, and other factors evident to those skilled in the art.

The pharmaceutical compositions containing a compound of formula I may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J. Pharm. Sci.* 73 (1964), 1294–1297, 1984; U.S. Pat. No. 4,489,056; and U.S. Pat. No. 4,210,644, which are incorporated herein by reference.

Examples of preferred compounds of formula I are centchroman as a racemic mixture and as l-centchroman and d-centchroman. Furthermore, 3,4-trans-2,2-dimethyl-3-phenyl-4-[4-(2-(pyrrolidin-1-yl)ethoxy)phenyl]-7-hydroxychroman is a preferred compound. A more preferred compound is d-3,4-trans-2,2-dimethyl-3-phenyl-4-[4-(2-(pyrrolidin-1-yl)ethoxy)phenyl)-7-methoxychroman The present invention is further illustrated by the following examples which, however, are not to be construed as limiting the scope of protection.

The features disclosed in the foregoing description and in the following examples may, both separately and in any combination thereof, be material for realising the invention in diverse forms thereof.

EXAMPLE

The effects of d-centchroman on arterial contractility was investigated in an in vitro system using thoracic aorta rings from female Wistar rats. The rats were killed and the thoracic aorta excised from the body and positioned in a small organ bath in which it was possible to measure contractility via a force transducer. Arterial contraction was induced by bathing the aorta ring in a solution containing 300 nM phenylephrine to which was added either increasing doses of vehicle (DMSO), estrogen or d-centchroman.

The data revealed (table 1) that d-centchroman possessed the ability to dilate a precontracted aorta ring. d-centchroman was a potent vasodilator with an $EC_{50}$ value of 13 μM approximately 5 times as potent as estrogen. Subsequent experiments in which the endothelial nitric oxide synthesis was blocked by l-NAME showed a rightward shift of the dose-response curve with a factor of about 10. These data indicated that at least some of the relaxing effect of d-centchroman is dependent on the synthesis of NO (endothelium derived relaxing factor, EDRF).

TABLE 1

Dose-response characteristics of compounds

| Compound | $EC_{50}$ ($\mu$M) | % Efficacy |
| --- | --- | --- |
| 17-β-estradiol | 60 | 57 |
| d-centchroman | 13 | 98 |

We claim:

1. A method for treatment or prophylaxis of tissue ischemia comprising administering to a patient in need of such treatment or prophylaxis an isolated 1-enantiomer of compound of formula I

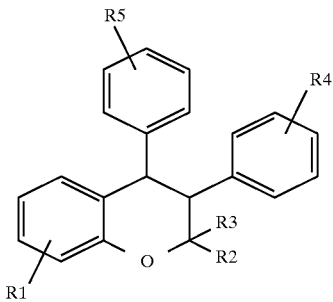

wherein R1, R4, and R5 are individually hydrogen, hydroxy, halogen, trifluoromethyl, lower alkyl, lower alkoxy or (tertiary amino) (lower alkoxy); and R2 and R3 are individually hydrogen or lower alkyl, or a pharmaceutically acceptable salt thereof in an amount sufficient to show a vasodilatory effect.

2. The method according to claim 1 ischaemia.

3. The method according to claim 1 in which said patient has angina pectons.

4. The method according to claim 1 in which said patient has Raynaud's syndrome.

5. The method according to claim 1 in which R1 is lower alkoxy.

6. The method according to claim 1 wherein R1 is methoxy.

7. The method according to claim 1 wherein R2 is lower alkyl.

8. The method according to claim 1 wherein R2 is methyl.

9. The method according to claim 1 wherein R3 is lower alkyl.

10. The method according to claim 1 wherein R3 is methyl.

11. The method according to claim 1 wherein R4 is hydrogen.

12. The method according to claim 1 wherein R5 is tertiary amino lower alkoxy.

13. The method according to claim 1 wherein said compound has the formula III:

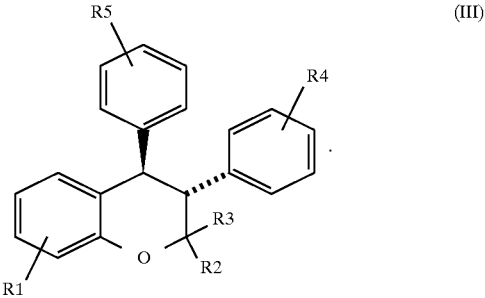

14. The method according to claim 1 wherein said compound is 3,4-trans-2,2-dimethyl-3-phenyl-4-[4-(2-(pyrrolidin-1-yl)ethoxy]-7-methoxychroman.

15. The method according to claim 1 wherein said compound is administered orally.

16. The method according to claim 1 wherein said compound is administered in a range from about 0.001 to 75 mg/kg patient per day.

17. The method according to claim 1 wherein said compound is administered in the form of dermal implant.

* * * * *

UNITED STATES PATENT AND TRADEMARK OFFICE
CERTIFICATE OF CORRECTION

PATENT NO. : 5,886,021
DATED : March 23, 1999
INVENTOR(S) : Shalmi, et. al.

It is certified that error appears in the above-identified patent and that said Letters Patent is hereby corrected as shown below:

Col. 1, line 10, change "snf" and insert --and--.
Col. 5, line 39, new claim 3, old claim 25, change "pectons" and insert --pectoris--.

Signed and Sealed this

Fourteenth Day of December, 1999

Attest:

Q. TODD DICKINSON

Attesting Officer

Acting Commissioner of Patents and Trademarks